United States Patent [19]
Gage et al.

[11] Patent Number: 5,770,414
[45] Date of Patent: Jun. 23, 1998

[54] REGULATABLE RETROVIRUS SYSTEM FOR GENETIC MODIFICATION OF CELLS

[75] Inventors: Fred H. Gage, La Jolla; Jasodhara Ray, San Diego, both of Calif.; Minoru Hoshimaru, Shiga-ken, Japan

[73] Assignee: The Regents of the University of California, Oakland, Calif.

[21] Appl. No.: 602,203

[22] Filed: Feb. 20, 1996

[51] Int. Cl.$^6$ ..................................................... C12N 15/00
[52] U.S. Cl. .................................... 435/172.3; 435/320.1; 435/353; 435/357
[58] Field of Search ................................. 435/320.1, 69.1, 435/69.2, 172.1, 172.3, 353, 240.2, 357; 935/22, 29, 32, 36, 41, 43, 57, 70

[56] References Cited

U.S. PATENT DOCUMENTS 5,464,758 11/1995 Gossen et al. ............................ 435/69.1
5,514,552 5/1996 Rosner et al. ........................... 435/7.21

OTHER PUBLICATIONS

Strair et al., "Retroviral mediated transfer and expression of exogenous genes in primary lymphoid cells: Assaying for a viral transactivator activity in normal and malignant cells", Blood 76(6): 1201–1208, Sep. 15, 1990.

Ryder, et al., Establishment and Characterization of Multipotent Neural Cell Lines Using Retrovirus Vector–Mediated Oncogene Transfer, *Journal of Neurobiology, 21*:356, 1990.

Bartlett, et al., Immortalization of Mouse Neural Precursor Cells by the c–myc Oncogene, *Proc. Natl. Acad. Acad. Sci. USA, 85*:3255, 1988.

Gossen, et al., Transcriptional Activation by Tetracyclines in Mammalian Cells, *Science, 268*:1766, 1995.

Snyder, et al., Multipotent Neural Cell Lines can Engraft and Participate in Development of Mouse Cerebellum, *Cell, 66*:33, 1992.

*Primary Examiner*—James Ketter
*Assistant Examiner*—Irem Yucel
*Attorney, Agent, or Firm*—Fish & Richardson, P.C.

[57] ABSTRACT

A novel regulatable retroviral vector in which the v-myc oncogene is driven by a tetracycline-controlled transactivator and a human cytomegalovirus minimal promoter fused to tet operator sequence useful for immortalization of adult neuronal progenitor cells is provided. Regulation of a heterologous Producer cell lines which produce high titers of the recombinant retrovirus are also provided.

19 Claims, 8 Drawing Sheets

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:1:

ATCGGTAAGC ACCGCAAGCA     20

( 2 ) INFORMATION FOR SEQ ID NO:2:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:2:

GGGAGCAACT CCATTCTTGT     20

( 2 ) INFORMATION FOR SEQ ID NO:3:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:3:

ACCTCGGCAC CCTGAGGCAG     20

( 2 ) INFORMATION FOR SEQ ID NO:4:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:4:

CCAGCGACTC AACCTTCCTC     20

( 2 ) INFORMATION FOR SEQ ID NO:5:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:5:

AAGGTTTTGG ACTTCCACCA C     21

( 2 ) INFORMATION FOR SEQ ID NO:6:

(i) SEQUENCE CHARACTERISTICS:
    (A) LENGTH: 21 base pairs
    (B) TYPE: nucleic acid
    (C) STRANDEDNESS: single
    (D) TOPOLOGY: linear (xi) SEQUENCE DESCRIPTION: SEQ ID NO:6:

CATAAGAACA AACACGGGTG C                                                   21

(2) INFORMATION FOR SEQ ID NO:7:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (xi) SEQUENCE DESCRIPTION: SEQ ID NO:7:

GAGGAGATAA CTGAGTACCG                                                     20

(2) INFORMATION FOR SEQ ID NO:8:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (xi) SEQUENCE DESCRIPTION: SEQ ID NO:8:

CCAAAGCCAA TCCGACACTC                                                     20

REGULATABLE RETROVIRUS SYSTEM FOR GENETIC MODIFICATION OF CELLS

STATEMENT AS TO FEDERALLY SPONSORED RESEARCH

This invention was made with support under Grant No. PO1 AG10435 from the National Institutes of Health. The government has certain rights in this invention.

FIELD OF THE INVENTION

The present invention is in the general field of neurobiology and generally relates to reagents useful for immortalization and/or differentiation of neuronal cells.

BACKGROUND OF THE INVENTION

Cells of the central nervous system (CNS) are broadly classified as either neurons or glial cells. Glial cells can be further subdivided into astrocytes and oligodendrocytes. Only a few CNS cell types have been reported to divide in the adult brain and do not survive well in vitro. Primary cultures tend to be heterogeneous in nature have been established by growth in fibroblast growth factor-2 (FGF-2). However, the generation of clonal cell lines from different regions of the brain, which can be further differentiated into neurons, is important and it may be necessary to immortalize cells with an oncogene to obtain such clonal lines.

There are hundreds of different types of cells in the CNS and many different neurotrophic factors which influence their growth and differentiation. Depending on the type of cell and the region of the brain in which the cell resides, a different neurotrophic factor or specific combination of factors affect the survival, proliferation and differentiation of the cell. Cells of the CNS may respond to different neurotransmitters, neurotrophic factors, and other molecules in its environment.

Recently, several researchers have isolated and immortalized progenitor cells from various regions of the brain and different stages of development. Olfactory and cerebellum progenitor cells have been immortalized using the viral myc (v-myc) oncogene to generate multipotent cell lines with both neuronal and glial phenotypes (Ryder, et al., *J Neurobiology*, 21:356, 1990). Similar studies by Snyder, et al. (*Cell*, 68:33,1992) resulted in multipotent neuronal cell lines which, when engrafted into the mouse cerebellum, differentiated into neurons and glial cells. These v-myc-immortalized cerebellar cell lines, established from the mouse external germinal layer (EGL), evinced different morphologies and different cell-type specific antigens, even within a given clone. In other studies, murine neuroepithelial cells were immortalized with a retrovirus vector containing c-myc and were induced to differentiate with growth factors to form differentiated cell types similar to glial cells and neuronal cells (Barlett, et al., *Proc. Natl. Acad. Sci. USA*, 85:3255,1988).

There is a need for a long-term in vitro culture system which would allow large scale production and maintenance of a CNS cell population, and particularly a neuronal progenitor cell line, which will proliferate and can be passaged and subcultured over time and can be induced to differentiate, if desired. Such homogenous in vitro cell cultures will prove invaluable in studying cell populations, the interactions between these cells, and the effects of various neuroactive compositions on these cells.

SUMMARY OF THE INVENTION

The present invention provides a novel regulatable retroviral vector useful for the production of recombinant retroviruses capable of infecting progenitor neuronal cells which can be cultured as progenitor cells or induced to differentiate. In a first aspect, the invention provides the vector, which is a regulatable vector including a heterologous gene, e.g., v-myc oncogene and regulatable nucleic acid sequences. For example, the vector is regulatable by addition of tetracycline. The invention also includes producer cell lines which produce recombinant retrovirus produced after transfection of a packaging cell line with the vector, or alternatively, produced after infection of a second packaging cell line with virus produced by a first packaging cell line. Also included are the immortalized progenitor neuronal cells produced by infection with the recombinant retrovirus of the invention.

Further, the invention provides a method for inducing differentiation of progenitor neuronal cells.

DESCRIPTION OF THE PREFERRED EMBODIMENTS

The present invention provides a regulatable retroviral vector useful for producing a recombinant retrovirus capable of infecting neuronal progenitor cells which can then be cultured as progenitor cells or induced to differentiate. The vector is a novel regulatable retroviral vector in which a heterologous gene's expression is regulated by a transactivator which regulates a promoter operably linked to the heterologous gene nucleic acid sequence. Recombinant retrovirus produced from the vector are useful for immortalization of neuronal progenitor cells and/or differentiation of such cells.

Retroviruses are RNA viruses in which the viral genome is RNA. When a host cell is infected with a retrovirus, the genomic RNA is reverse transcribed into a DNA intermediate which is integrated very efficiently into the chromosomal DNA of infected cells. This integrated DNA intermediate is referred to as a provirus. Transcription of the provirus and assembly into infectious virus occurs in the presence of an appropriate helper virus or in a cell line containing appropriate sequences enabling encapsidation without coincident production of a contaminating helper virus.

The retroviral genome and the proviral DNA have three genes:. the gag, the pol, and the env, which are flanked by two long terminal repeat (LTR) sequences. The gag gene encodes the internal structural (matrix, capsid, and nucleocapsid) proteins; the pol gene encodes the RNA-directed DNA polymerase (reverse transcriptase) and the env gene encodes viral envelope glycoproteins. The 5' and 3' LTRs serve to promote transcription and polyadenylation of the virion RNAs. The LTR contains all other cis-acting sequences necessary for viral replication.

The recombinant retrovirus of the invention is genetically modified in such a way that some of the structural, infectious genes of the native virus have been removed and replaced instead with a nucleic acid sequence to be delivered to a target cell. After infection of a cell by the virus, the virus injects its nucleic acid into the cell and the retrovirus genetic material can integrate into the host cell genome. The transferred retrovirus genetic material is then transcribed and translated into proteins within the host cell.

In a first aspect, the invention provides a retroviral vector with nucleic acid encoding a regulatory transactivator element; an optional internal ribosome entry site (IRES); a selectable marker, a regulatory element in operable linkage with a heterologous gene; heterologous gene nucleic acid sequences and cis-acting nucleic acid sequences necessary for reverse transcription and integration.

The heterologous nucleic acid sequence is operably linked to a regulatory nucleic acid sequence, e.g., promoter sequence. As used herein, the term "heterologous" nucleic acid sequence refers to a sequence that originates from a foreign species, or, if from the same species, it may be substantially modified from its original form. Alternatively, an unchanged nucleic acid sequence that is not normally expressed in a cell is a heterologous nucleic acid sequence. The heterologous gene is typically an oncogene, such as v-myc, when it is desirable to immortilize the progenitor cells for long term tissue culture. Alternatively, the heterologous gene may encode a protein product important in normal neuronal cell function, e.g., tyrosine hydroxylase in the production of dopamine; choline acetyl transferase for the production of acetylcholine. It is envisioned that any heterologous gene can be cloned into the vector of the invention for genetic modification of a cell.

The promoter in operable linkage with the heterologous gene can be any viral or housekeeping gene promoter, including for example, cytomegalovirus (CMV) LTR, DHFR, SV40 immediate early gene, Moloney murine leukemia virus and Rous Sarcoma virus LTR promoter. The promoter sequence may be homologous or heterologous to the nucleic acid sequence. A wide range of promoters may be utilized, including viral or tissue specific promoter. Cell or tissue specific promoters can be utilized to target expression of gene sequences in specific cell populations. Suitable mammalian and viral promoters for the present invention are available in the art. However, the promoter operably linked with the heterologous gene must be responsive to the regulatable transactivating element.

Figure 1:
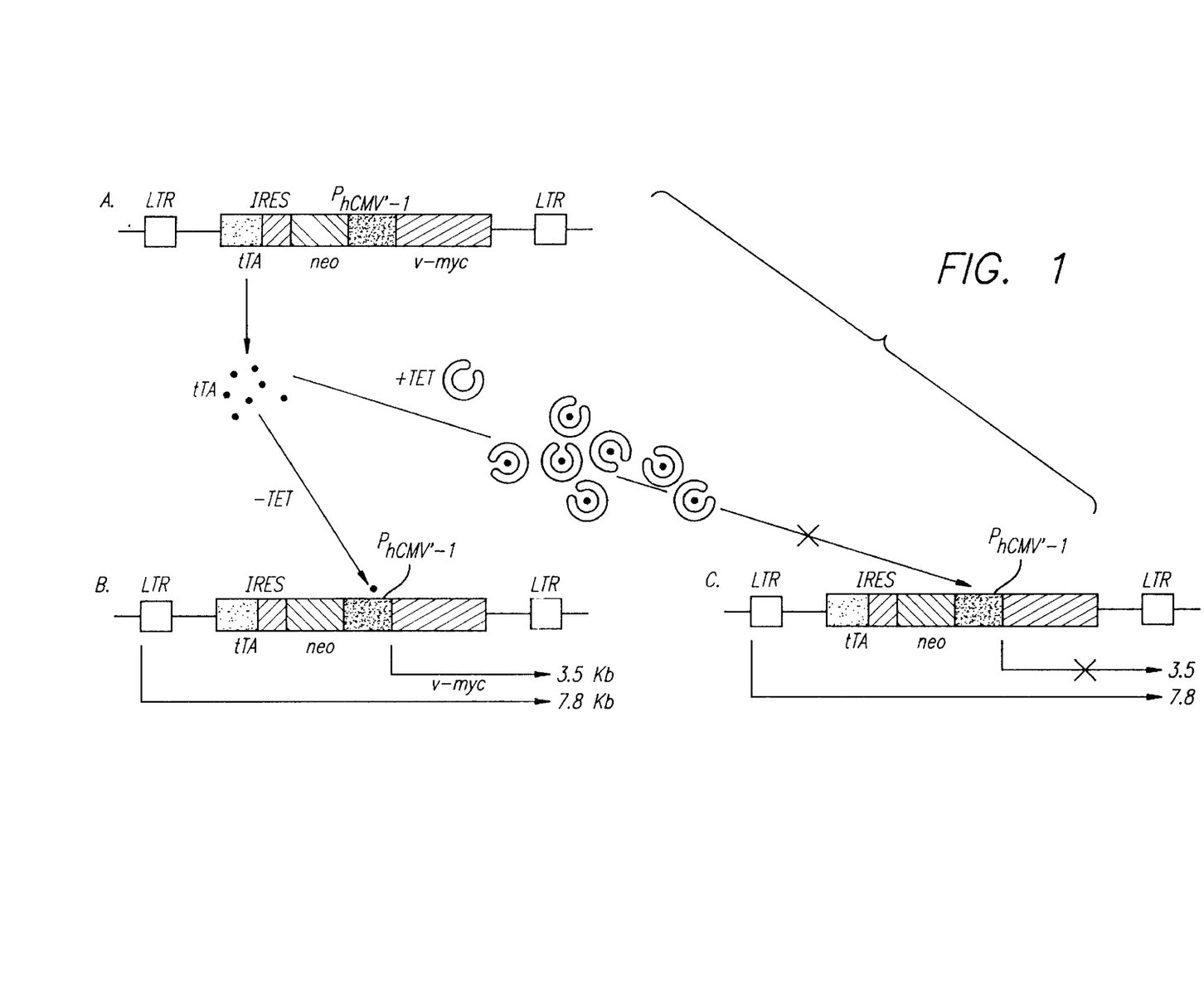
FIG. 1A shows an illustration of the structure of LINXv-myc, the exemplary vector of the invention. Long terminal repeat (LTR); tetracycline-controlled transactivator (tTA); neomycin phosphotransferase (neo); encephalomyocarditis virus internal ribosome entry site (IRES); tTA-dependant promoter ($P_{hCMV^{*}-1}$).
FIG. 1B shows an illustration of the 3.5 kb v-myc mRNA, which is transcribed in the absence of tetracycline.
FIG. 1C shows an illustration depicting inhibition of tTA-induced transcription of the 3.5 kb v-myc mRNA in the presence of tetracycline.

In a preferred embodiment, retroviral vector nucleic acid encodes a tetracycline controlled transactivator (tTA); an internal ribosome entry site (IRES); a selectable marker; a human cytomegalovirus (hCMV) promoter in operable linkage to tetracycline operator; v-myc; and cis-acting nucleic acid sequences necessary for reverse transcription and integration. An illustration of a representative vector of the invention is shown in FIG. 1A and is deposited as ATCC 69991 (American Type Culture Collection, Rockville, Md. 20852).

As used herein, the term "operable linkage" refers to functional linkage between a promoter sequence and the structural gene regulated by the promoter nucleic acid sequence. The operably linked promoter controls the expression of the polypeptide encoded by the structural gene, or in a preferred embodiment of the invention, the heterologous gene nucleic acid sequences. The orientation or placement of the elements of the vector is not strict, so long as the "operable linkage" requirement is fulfilled for control of and expression of the nucleic acid sequences.

The control elements of tet-resistance operon encoded in *E. coli* transposon 10, for example, are utilized in the production of the tetracycline-regulatable vector system. In the exemplified vector of the invention, the prokaryotic tet repressor was converted to a eukaryotic transactivator by fusion of the repressor with the activating domain (C-terminal) of Herpes simplex virus VP16 protein. This transactivator strongly activates transcription from the minimal promoter $P_{hCMV^*-1}$, fused to tet operator sequences (Gossen, et al., Proc. Natl. Acad. Sci USA, 89:5547, 1992). Synthesis of tetracycline controlled transactivator (tTA) activates $P_{hCMV^*-1}$ promoter and v-myc oncogene is expressed from this promoter in a tetracycline-regulated manner. The long terminal repeat (LTR) of Moloney murine sarcoma virus is preferably used for transcription of mRNA containing both tTA and neomycin phosphotransferase gene (neo) by means of an internal ribosome entry site (IRES). Other viral LTRs can be used and will be well known to those of skill in the art.

Other selectable marker genes that can be used in place of neo include for example, aminoglycoside phosphotransferase, dihydrofolate reductase (DHFR), hygromycin-B-phosphotransferase (HPH), and xanthine guanine phosphoribosyltransferse (XGPRT, gpt).

As used herein, the term "regulatable" means that an element is activated in a negative manner, or "down-regulated", or in a positive manner, or "up-regulated". The preferred vector is tet-regulatable in that a low concentration of tetracycline abolishes transcriptional activation by tTA, in other words tTA is "down-regulated". This in turn suppresses heterologous gene expression (e.g., v-myc) from the operably linked promoter of the heterologous gene and for example, allows progenitor cells to terminally differentiate into neurons. Other similar regulatable transactivating elements analagous to the tetracycline system described herein will be known to those of skill in the art. Similarly, the transcriptional activator can be "up-regulated", resulting in increased expression of the heterologons gene. For example, a mutant tet repressor can be inserted as the regulatable tTA, in order to induce v-myc expression. (See for example, Gossen, et al, *Science*, 268:1766, 1995, incorporated herein by reference).

The vector of the invention is used to produce recombinant retrovirus which can be used to infect neuronal progenitor cells. Therefore, in another aspect of the invention, a suitable packaging host cell line is transfected with the vector of the invention in order to produce packaged viral particles. The retrovirus vector of the invention does not encode the structural genes whose products comprise the viral particle. To produce infectious viral particles from a retrovirus plasmid, the viral structural proteins encoded by gag, pol, and env are supplied by packaging cell lines. The vector contains the packaging sequence, Ψ, therefore, vector RNA is preferentially packaged.

Since recombinant retroviruses produced by standard methods in the art are defective, they require assistance in order to produce infectious vector particles. Typically, this assistance is provided, for example, by using a helper packaging cell line that provides the missing viral functions. These plasmids are missing a nucleotide sequence which enables the packaging mechanism to recognize an RNA transcript for encapsidation.

Helper cell lines which have deletions of the packaging signal include but are not limited to murine ecotropic lines such as Psi-2 (Ψ2), ΨCRE, GP+E-86, and ΩE, murine amphotropic lines such as PA317, PA12, Ψam, and ΨCRIP, for example (see *Current Protocols in Molecular Biology*, Vol. 1, 1995, ed. Ausubel et al., Greene Publish. Assoc. & Wiley Interscience, Ch. 9). Suitable cell lines produce empty virions, since no genome is packaged. If a retroviral vector is introduced into such cells in which the packaging signal is intact, but the structural genes are replaced by other genes of interest, the vector can be packaged and vector virion produced.

An infectious virus stock is made from the cloned vector encoded by a plasmid in the preferred vector of the invention, by transfecting the retrovirus vector plasmid into a packaging cell line for replication incompetent vectors. Once the vector is in the cell line, transcription proceeds from the viral LTR promoter encoded by the plasmid, generating an RNA viral genome. The viral genome is then encapsidated by viral structural proteins and infectious viral particles are produced by budding from the surface of the cells. The supernatant produced by the cells comprises a virus stock.

The packaging cell line can be used for the production of virus, however, it is preferable to produce a stable producer cell line for a continual source of high-titer virus stocks. One could select among the transfected packaging cells for those that have stably integrated the vector plasmid. They can be placed under drug selection and the resulting drug-resistant cells screened for virus production. Alternatively, a "cross infection" can be performed by taking transiently produced virus harvested from the packaging cell line as described above, and used to infect another packaging line. The infected packaging cells can then be placed under drug selection. For example, in the present method of the invention, the packaging cell line Psi-2 was originally transfected and virus produced by this cell line were used to infect the amphotropic cell packaging cell line, PA317. Cells were selected for G418 resistance and colonies selected for production of v-myc and high titer of recombinant retrovirus.

In one embodiment, the invention includes the packaging cell line which produces the packaged virus produced as described above, as well as the packaged recombinant retrovirus itself The first or second packaging cell line which produces virus is also referred to as a "producer" cell line. Therefore, the present invention includes both a packaging cell line comprising the vector described herein, as well as a producer cell line which produces infectious recombinant retrovirus as described herein. An exemplary producer cell line of the present invention is described in Example 2. Other producer cell lines can be produced utilizing the method described therein and the vector of the invention. In another embodiment, the invention includes the recombinant retrovirus produced by the producer cell line. It should be understood that the recombinant retrovirus of the invention is capable of infecting any cell type, both fetal and adult, and not just neuronal progenitor cells.

The invention also provides a method for introduction and expression of a heterologous nucleic acid sequence in a neuronal progenitor cell comprising infecting the cell with the recombinant virus of the invention and expressing the heterologous nucleic acid sequence in the cell. Thus, the invention provides a general method for genetic modification of cells, including neuronal progenitor cells. For example, introduction of an oncogene, such as v-myc, allows immortalization of neuronal progenitor cells which can then be cultured over a long period of time while expressing the v-myc gene. Alternatively, cells can be genetically modified to express a gene for specific production of the gene product, e.g. tyrosine hydroxylase.

The invention also provides a method for inducing differentiation of neuronal progenitor cells comprising infecting a progenitor neuronal cell with a retrovirus produced by the producer cell line as described above, and growing the cells under conditions and for a suitable time to allow the cells to differentiate.

Cells are grown under culture conditions (e.g., appropriate media, serum, growth factors), as discussed below, and for a suitable time for induction of differentiation. One of skill in the art could readily determine whether or not a neuronal progenitor cell has differentiated. For example, various precursor neuronal cell markers such as vimentin and nestin, will be present in undifferentiated cells and absent in differentiated cells. In contrast, cell markers such as tau, NeuN, glutamic acid decarboxylase, and neurofilament 200 kD protein (NFH) are indicative of differentiated neurons. Immunological or molecular biological (e.g., Northern blot) techniques can be used to identify neuronal cell markers.

Cells can also be analyzed for differentiation by expression of large sodium and calcium currents which fire regenerative action potentials (see EXAMPLE 5).

There are hundreds of different types of cells of the nervous system, each with distinct properties. Each type of cell produces and responds to different combinations of neurotransmitters and neurotrophic factors. Cells of the nervous system do not divide in the adult brain, nor do they generally survive long in vitro without treatment or growth factors. The method of the invention therefore provides for the production of long term cultures of progenitor cells. The neuronal progenitor cells which can be used for induction of differentiation into neurons can be isolated from virtually any region of the brain and spinal cord (Palmer, et al., *Mol. Cell. Neurosci.*, 6:476, 1995). Either embryonic or adult tissue can be utilized. A "progenitor cell" is a dividing cell capable of self renewal and capable of differentiation into many cell types, including adult neurons.

The tissue containing progenitor neurons can be derived from any fetal or adult neural tissue, including tissue from the hippocampus, cerebellum, spinal cord, cortex (e.g., motor or somatosensory cortex), striatum, basal forebrain (cholinergic neurons), ventral mesencephalon (cells of the substantia nigra), and the locus ceruleus (neuroadrenaline cells of the central nervous system), and hypothalamus. Example 3 domonstrates immortalization of adult cells; the same technique was used to immortalize fetal cells.

The liquid media for culture of a neuronal progenitor cell of the invention is supplemented with growth factors such as basic fibroblast growth factor, to support the growth and proliferation of a neuronal progenitor cell.

In addition to interactions with soluble factors, most cells in vivo, including neuron cells, are in contact with an extracellular matrix, a complex arrangement of interactive protein and polysaccharide molecules which are secreted locally and assemble into an intricate network in the spaces between cells. Therefore, the addition of an extracellular matrix protein to the surface of the culture vessel forms an insoluble matrix which allows neural cells in culture to adhere in a manner which closely corresponds to the in vivo extracellular matrix The cell of the invention can be preferably produced by coating the surface of a vessel, such as a tissue culture dish or flask, with a polybasic amino acid composition to allow initial attachment. Such compositions are well known in the art and include polyornithine and polylysine. Most preferably, the polybasic amino acid of the invention is polyornithine. Additionally, the surface of the vessel may be coated with a known extracellular matrix protein composition to enhance the neuronal cell's ability to grow and form processes on the substrate. Such compositions include laminin, collagen and fibronectin. Other extracellular matrix proteins that can be used in conjunction with a polybasic amino acid will be apparent to one of skill in the art.

The neuronal progenitor cell of the invention or differentiated neuron cell is useful as a screening tool for neuropharmacological compounds which affect a biological function of the neuron. Thus, in another embodiment, the invention provides a method for identifying a composition which affects a neuron by incubating the components, which include the composition to be tested and the neuron, under conditions sufficient to allow the components to interact, then subsequently measuring the effect of the composition on the neuron. The observed effect on the neuron may be either inhibitory or stimulatory. For example, a neuroactive compound which mimics a neurotransmitter or binds to a receptor and exhibits either an antagonistic or agonist effect, thereby inhibiting or stimulating a biological response in the neuron, can be identified using the method of the invention. The occurrence of a biological response can be monitored using standard techniques known to those skilled in the art. For example, inhibition or stimulation of a biological response may be identified by the level of expression of certain genes in the neuron. Such genes may include early response genes such as fos, myc or jun (Greenberg, M. and Ziff, E. *Nature*, 311:433, 1984; eds. Burck, et al, in *Oncogenes*, 1988, Springer-Verlag, N.Y.). Other genes, including those which encode cell surface markers can also be used as indicators of the effects neuropharmacological compounds on the neurons of the invention. Methods for measurement of such effects include Northern blot analysis of RNA (transcription), SDS-PAGE analysis of protein (translation), [$^3$H]-thymidine uptake (DNA synthesis) and antibody reactivity (both intracellular and extracellular). Other commonly used methods will be apparent to those of skill in the art.

Neuroactive drugs which act similarly to those already known to affect neuronal cells can thus be identified. For example, new drugs that alleviate anxiety, analogously to Valium, which augment or stimulate the action of the important inhibitory transmitter gamma-aminobutyric acid (GABA), can be identified. Antidepressants, such as Prozac, enhance the action of serotonin, an indoleamine with a wide variety of functions. Other drugs can be readily identified using the neurons according to the method of the invention. Other examples include psychoactive compounds. For example, cocaine facilitates the action of dopamine, whereas certain antipsychotics antagonize or inhibit this catecholamine. Another example is nicotine which activates the acetylcholine receptors which are distributed throughout the cerebral cortex. Therefore, by using neurons derived from neuronal progenitor cells from the appropriate regions of the brain, drugs and trophic factors which bind various receptors and would produce similar effects on neuronal cells can be identified.

The present invention also provides a method of treating a subject with a neuronal cell disorder by administering to the subject a therapeutically effective amount of a neuronal progenitor cell. "Therapeutically effective" as used herein, refers to that amount of neuron that is of sufficient quantity to ameliorate the cause of the neuronal disorder. "Ameliorate" refers to a lessening of the detrimental effect of the neuronal disorder in the patient receiving the therapy. For example, in a patient with Parkinson's disease, it may be desirable to administer a therapeutically effective amount of cells producing tyrosine hydroxylase. The subject of the invention is preferably a human, however, it can be envisioned that any animal with a neuronal disorder can be treated with the neuron of the invention. Preferably, the original progenitor neuronal cells are derived from neuronal tissue of the same species as the species of the subject receiving therapy.

The method of treating a subject with a neuronal disorder entails intracerebral grafting of neuronal progenitor cells to the region of the CNS having the disorder. Where necessary, the neuronal progenitors can be genetically engineered to contain an exogenous gene. The disorder may be from either disease or trauma (injury). Neuronal progenitor cell transplantation, or "grafting" involves transplantation of cells into the central nervous system or into the ventricular cavities or subdurally onto the surface of a host brain. Such methods for grafting will be known to those skilled in the art and are described in *Neural Grafting in the Mammalian CNS*, Bjorklund and Stenevi, eds., (1985), incorporated by reference herein. Procedures include intraparenchymal transplantation, (i.e., within the host brain) achieved by injection or deposition of tissue within the host brain so as to be apposed to the brain parenchyma at the time of transplantation.

Administration of the neuronal progenitor cells of the invention into selected regions of the recipient subject's brain may be made by drilling a hole and piercing the dura to permit the needle of a microsyringe to be inserted. The neuronal progenitor cells can alternatively be injected intrathecally into the spinal cord region. The neuronal progenitor cell preparation of the invention permits grafting of these cells to any predetermined site in the brain or spinal cord, and allows multiple grafting simultaneously in several different sites using the same cell suspension and permits mixtures of cells from different anatomical regions. The present invention provides a method for transplanting various neural tissues, by providing previously unavailable proliferating neuronal progenitor cells and a culture system for production of these neuronal progenitor cells in order to grow a sufficient number of cells for in vitro gene transfer followed by in vivo implantation.

The neuronal progenitor cells produced by the method of the invention used for treatment of a neuronal disorder may optionally contain an exogenous gene, for example, an oncogene, a gene which encodes a receptor, or a gene which encodes a ligand. Such receptors include receptors which respond to dopamine, GABA, adrenaline, noradrenaline, serotonin, glutamate, acetylcholine and other neuropeptides, as described above. Examples of ligands which may provide a therapeutic effect in a neuronal disorder include dopamine, adrenaline, noradrenaline, acetylcholine, gamma-aminobutyric acid and serotonin. The diffusion and uptake of a required ligand after secretion by a donor neuronal progenitor cell would be beneficial in a disorder where the subject's neural cell is defective in the production of such a gene product. A neuronal progenitor cell genetically modified to secrete a neurotrophic factor, such as nerve growth factor, (NGF), might be used to prevent degeneration of cholinergic neurons that might otherwise die without treatment. Alternatively, neuronal progenitor cells to be grafted into a subject with a disorder of the basal ganglia, such as Parkinson's disease, can be modified to contain an exogenous gene encoding L-DOPA, the precursor to dopamine. Parkinson's disease is characterized by a loss of dopamine neurons in the substantia nigra of the midbrain, which have the basal ganglia as their major target organ. Alternatively, neurons derived from substantia nigra neuronal cells which produce dopamine could be introduced into a Parkinson's patient brain to provide cells which "naturally" produce dopamine.

Other neuronal disorders that can be treated similarly by the method of the invention include Alzheimer's disease, Huntington's disease, neuronal damage due to stroke, and damage in the spinal cord. Alzheimer's disease is characterized by degeneration of the cholinergic neurons of the basal forebrain. The neurotransmitter for these neurons is acetylcholine, which is necessary for their survival. Engraftment of cholinergic neurons, or neurons containing an exogenous gene for a factor which would promote survival of these neurons can be accomplished by the method of the invention, as described. Following a stroke, there is selective loss of cells in the CA1 of the hippocampus as well as cortical cell loss which may underlie cognitive function and memory loss in these patients. Once identified, molecules responsible for CA1 cell death can be inhibited by the methods of this invention. For example, antisense sequences, or a gene encoding an antagonist can be transferred to a neuronal progenitor and implanted into the hippocampal region of the brain.

The method of treating a subject with a neuronal disorder also contemplates the grafting of neuronal progenitors in combination with other therapeutic procedures useful in the treatment of disorders of the CNS. For example, the neuronal progenitors can be co-administered with agents such as growth factors, gangliosides, antibiotics, neurotransmitters, neurohormones, toxins, neurite promoting molecules and antimetabolites and precursors of these molecules such as the precursor of dopamine, L-DOPA.

The following examples are intended to illustrate but not limit the invention. While they are typical of those that might be used, other procedures known to those skilled in the art may alternatively be used.

EXAMPLES

Vector Construction

The retroviral vector LINXv-myc was constructed as follows: the 1.02 kb EcoRI-BamHI fragment of the tTA was excised from pUHD15-1 (Gossen, et al., *Proc. Natl. Acad. Sci. USA*, 89:5547, 1992) and inserted into pHENA (Palmer, et al., *Nucl. Acids Re.*, 21:3451, 1993) just upstream of the internal ribosome entry site (IRES) of the encephalomyocarditis virus. The resultant 2.78 kb EcoRV-BamHI fragment containing tTA, IRES and neomycin phosphotransferase was inserted into the polylinker site (HapI and BamHI) of LXSHD (Stockschlaeder, et al., *Human Gene Therapy*, 2:33, 1991). Then, the portion of LXSHD spanning SV40 early promoter and histidinol dehydrogenase cDNA was replaced by $P_{hCMV^*-1}$-v-myc (3.32 kb) fragment. $P_{hCMV^*-1}$ was derived from pUHD10-3 and 2.87 kb SacI-SphI fragment of v-myc was derived from pMC38 (ATCC, Rockville, Md). The exemplary vector was deposited with the American Type Culture Collection in Rockville, Md., USA, prior to the filing date of the present application.

The following cell line has been deposited with the American Type Culture Collection, 1301 Parklawn Drive, Rockville, Md., 20852, USA (ATCC) on Feb. 16, 1996:

| Cell line (culture) | ATCC Accession No. |
|---|---|
| LINX v-myc | 69991 |

The deposit was made under the provisions of the Budapest Treaty on the International Recognition of the Deposit of Microorganisms for the Purpose of Patent Procedure and the Regulations thereunder (Budapest Treaty). Applicant assures maintenance of viable cultures for 30 years from the date of deposit. The organisms will be made available by ATCC under the terms of the Budapest Treaty which assures permanent and unrestricted availability of the progeny of the culture to the public upon issuance of the pertinent U.S. patent or upon laying open to the public of any U.S. or foreign patent application, whichever comes first, and Applicant assures availability of the progeny to one determined by the U.S. Commissioner of Patents and Trademarks to be entitled thereto according to 35 USC § 122 and the Commissioner's rules pursuant thereto (including 37 CFR § 1.14 with particular reference to 886 OG 638).

If the culture deposit should die or be lost or destroyed when cultivated under suitable conditions, it will be promptly replaced on notification with a viable specimen of the same culture. Availability of a deposited strain is not to be construed as a license to practice the invention in contravention of the rights granted under the authority of any government in accordance with its patent laws.

Cell Culture

All packaging and producer cell lines were cultured in Dulbecco's modified Eagle's medium (DMEM) with 10% fetal bovine serum. Psi-2 cells were transfected with 10 $\mu$g of LINXv-myc plasmid DNA by standard calcium phosphate procedure. Virus-containing medium collected from Psi-2 cells two days after transfection was used to infect the amphotropic PA317 cells. One day after the infection, the cells were split at 1:10 ratio, plated and selected for G418 (400 μg/ml) resistance. Colonies were picked after selection for eight days and tested for the proper integration of the vector, production of v-myc and the titer of the retrovirus.

Cells from adult (3-month-old) rat hippocampus were isolated and cultured as described previously (Ray, J. and Gage, F., *J Neurosci.*, 14:3548, 1994) with the following modifications. Cells isolated from tissue after enzymatic dissociation were resuspended into DMEM:F-12 (1:1) high glucose medium (Irvine Scientific) containing 10% fetal bovine serum and then plated onto uncoated plastic tissue culture flasks ($1 \times 10^6$ cells/75 cm² flask). The cells were grown at 37° C. in 5% $CO_2$ incubator. The following day, the serum containing medium was replaced with serum free DMEM:F12 medium containing N2 supplement (5 μg/ml insulin, 50 μg/ml human transferrin, 20 nM progesterone, 100 μM putrescine, 30 nM Na selenite, 2.5 mM glutamine; GIBCO) and 20 ng/ml FGF-2 (human recombinant). Confluent cultures of cells were passaged to polyomithine/laminin-coated plates and cultured. Proliferating cultures, maintained for about a year through 19 passages were split at a 1:3 ratio and one day later infected for 20 hours with a mixture of one volume of the conditioned media of the producer cell line and two volumes of DMEM:F 12 containing N2 supplements, 20 ng/ml FGF-2 and 4 μg/ml polybrene. The infected cells were split at a 1:4 ratio and selected in the presence of G418 (100 μg/ml).

Northern Blot Analyses

Total RNA was isolated by CsCl-guanidinium thiocyanate method (Ausubel, et al, *Short Protocols in Molecular Biology*, pp. 142, 1989). Fifteen μg of total RNA was separated on formaldehyde-agarose (1.5%) gels and transferred onto Magnagraph nylon membrane and probed with randomly primed v-myc or cyclophilin (pB1B15).

Immunofluorescence Staining

Cells were plated in the absence or presence of tetracycline (1 μg/ml) onto Lab-Tek glass chamber slides (Nunc) coated with polyornithine/laminin and cultured for one (without tetracycline) or five days (with tetracycline) and then fixed for 10 minutes with 4% paraformaldehyde. The cells were incubated sequentially with the primary antibody in PBS containing 4% donkey serum and 0.3% Triton X-100 overnight at 4° C. followed by fluorescein (FITC)-conjugated secondary antibody (Jackson Immunoresearch Laboratories, Inc.; used at 1:500) for 4 hours at room temperature. Slides were mounted in 24% glycerol and 9.6% polyvinyl alcohol containing 2.5% 1.4-diazobycyclo[2.2.2] octane. The monoclonal antibodies used were to tau (Boehringer Mannheim: used at 1:250), neurofilament 200 kDa (NFH)(clone RT97; Boehringer Mannheim; used at 2 mg/ml), NeuN (used at 1:5; Mullen, et al., *Development*, 116:201, 1992) and polyclonal antibodies to vimentin (Amersham; used at 1:10), glial fibrillary acidic protein (GFAP) (Chemicon International; used at 1:2000), nestin (used at 1:10,000) and v-myc (Upstate Biotechnology Inc.; used at 1:8000). For immunofluorescent staining for bromodeoxyuridine (BrdU), cells were incubated with BrdU (Amersham; used at 1:1000) for 18 hours, fixed with 95% ethanol/5% acetic acid and then incubated with monoclonal anti-BrdU antibody (Amersham; undiluted). Immunoreactivity was detected with anti-mouse biotinylated IgG followed by streptavidin-Texas red conjugate.

Confocal microscopic images of cells were obtained using a BioRad MRC600 confocal microscope equipped with a krypton/argon laser and coupled to a Zeiss Axiovert microscope. Images were collected sequentially using the K1/K2 filter blocks matched to the appropriate excitation filter for each channel. Transmitted light images of differential interference contrast optics were captured in registration with the fluorescent signals using the transmitted field detector. Instrument settings to preclude background fluorescent signals were set against a negative control well where the primary antibodies had been omitted; gain and black levels were adjusted to preclude any signal from this well before imaging other wells for positive signal. Collected digital images were compositied in Adobe Photoshop 3.0 and printed on a Fujix Pictrography 3000. Phase contrast images were photographed on a Nikon Diaphot using T-Max film and the negatives digitized using a Leaf Lumina. These images were printed as described above.

RT-PCR Analysis

One hundred nanograms of total RNA was reverse transcribed using avian myeloblastosis virus reverse transcriptase (Promega) with random hexamers (10 μM) as primers in a 20 ml reaction mixture containing 10 mM Tris-Cl (pH 8.4), 50 mM KCl, 3.8 mM $MgCl_2$, 1 mM each dATP, dTTP, dCTP, dGTP, and 20U of RNasin (Promega). After 75 min at 42° C., the reaction was determined by heat inactivation at 95° C. for 5 min. For PCR amplification, several sets of specific oligonucleotide pairs (10 ng/μl) were incubated with the above reaction mixture and 5 units of Taq polymerase (Perkin Elmer) in a 100 μl reaction mixture containing 10 mM Tris-Cl (pH 8.4), 50 mM KCl, 1 mM $MgCl_2$, and 2 μCi [$\alpha$-$^{32}$P]dCTP. Cycle parameters were 2 min at 94° C., 2 min at 60° C., and 2 min at 72° C. for 23 cycles followed by a final 10 min incubation at 72° C. Forty microliters of each reaction were analyzed by electrophoresis on 8% polyacrylamide gels followed by autoradiography. Control experiments using primers for the rat ribosomal protein L27a (internal control) showed that the amount of amplified PCR product was directly proportional to the amount of input RNA after 23 cycles of amplification. The sequences of genomic DNA between two primers were selected so that they contained one or two introns for discrimination between products from RNA and contaminating genomic DNA. The following oligonucleotides were used as primers (nucleotide positions are shown in parentheses): rat ribosomal protein L27a (Wool, et al., *Biochem Biophys. Acta*, 1050:69, 1990) 5' primer:5'-ATCGGTAAGCACCGCAAGCA-3'(69–88)(SEQ ID NO:1); 3'primer:5'-GGGAGCAACTCCATTCTTGT-3' (302–283)(SEQ ID NO:2); rat GFAP (Wool, et al., *Biochem. Biophys. Acta.*, 1050:69, 1990) 5'primer:5'-ACCTCGGCACCCTGAGGCAG-3'(459–478)(SEQ ID NO:3); 3'primer:5'-CCAGCGACTCAACCTTCCTC-3' (599–580)(SEQ ID NO:4); rat glutamic acid decarboxylase (GAD)(Wyborski, et al, *Mol. Brain Res.*, 8:193, 1990) 5' primer:5'-AAGGTTTTGGACTTCCACCAC-3'(589–609) (SEQ ID NO:5); 3' primer:5'-CATAAGAACAAACACGGGTGC-3'(855–835)(SEQ ID NO:6); rat NFH (Breen, et al., *FEBS Lett.*, 241:213, 1988), 5' primer:5'-GAGGAGATAACTGAGTACCG-3'(247–266) (SEQ ID NO:7); 3' primer:5'-CCAAAGCCAATCCGACACTC-3'(548–529)(SEQ ID NO:8).

Electrophysiology

The whole-cell configuration of the patch clamp technique was used to study voltage-gated currents. Pipettes (3- to 5-MΩ resistance) were pulled from Boralex glass (Rochester Scientific Co.), coated with Sylgard (Dow Corning Corp.) and fire-polished. They were filled with internal solution containing 108 mM cesium methanesulfonate, 4 mM $MgCl_2$, 9 mM EGTA (ethylene glycol bis(b-aminoethyl ether)-N,N,N',N'-tetraacetic acid), 9 mM HEPES [4-(2-hydroxyethyl)-1-piperazineethanesulfonic acid], 4 mM ATP, 14 mM creatine phosphate (Tris salt), 0.3 mM GTP (Tris salt) and 50 U/ml creatine phosphokinase, pH 7.4 with CsOH. Whole-cell recordings were initially established in the bath solution (Tyrode's: 150 mM NaCl, 4 mM KCl, 2 mM $MgCl_2$, 10 mM glucose, 10 mM HEPES, pH 7.4 with NaOH; 2 mM $CaCl_2$ and, in some cases, 4 mM $BaCl_2$ added). Sodium currents were characterized in this bath solution, whereas calcium currents were assessed with external solution containing 160 mM tetraethyl ammonium chloride (TEA-Cl), 10 mM $BaCl_2$, and 10 mM HEPES, pH 7.4 with TEA-OH, 1 $\mu$M tetrodotoxin (TTX, Sigma) added. External solutions flowed from an array of microcapillary tubes (internal diameter 140 $\mu$m), driven by gravity; solution exchange was complete in less than 500 msec.

Whole-cell currents were recorded using an Axopatch 200A patch clamp amplifier and the BASIC-FASTLAB interface system (INDEC Systems). Voltage-dependent currents were filtered at 10 KHz (4-pole Bessel low-pass) and digitized every 25 $\mu$s (sodium current) or 50 $\mu$s (calcium current). Series resistance compensation was employed, typically for 80–95% of the series resistance measured from the uncompensated capacity transient (dividing the decay time constant by cell capacitance) or from the potentiometer used for nulling the capacity transient. Data were accepted for sodium and calcium current only if the remaining voltage error (calculated as current times uncompensated series resistance) was less than 1 mV, and if voltage control was adequate as judged by a graded increase in a peak current as test depolarizations were increased. Reported potentials have been corrected for a liquid junction potential of –10 mV between the internal solution and the Tyrode's solution in which the pipette current was zeroed before sealing onto the cell. Sodium and calcium channel currents were corrected for leak and capacitative currents by subtraction of an appropriately scaled current elicited by a hyper-polarization from –80 mV to –90 mV. All experiments were done at 21°–25° C. Statistics are given as mean ±SEM.

Example 2

Generation of a Producer Cell Line

The control elements of tet-resistance operon in *E. coli* transposon 10 have been used to generate a tetracycline-regulatable vector system (Gossen, et al., supra, 1992; Gossen, et al., *Trends Biochem. Sci.*, 18:471, 1993). In this vector, the prokaryotic tet repressor was converted to a eukaryotic transactivator by fusion of the repressor with the activating domain (C-terminal) of herpes simplex virus VP16 protein. This transactivator strongly activates transcription from the minimal promoter $P_{hCMV^*-1}$ fused to tet operator sequences (Gossen, et al, supra, 1992). Although this promoter has a very low basic activity in HeLa cells or in most tissues of transgenic mice, the synthesis of tTA activates $P_{hCMV^*-1}$ promoter (Gossen, et al., supra, 1992; Gossen, et al., supra, 1993; Efrat, et al., *Proc. Natl. Acad. Sci. USA*, 92:3576, 1995; Furth, et al., *Proc. Natl. Acad. Sci USA*, 91:9302, 1994). Using this vector system, a retroviral vector was constructed to express v-myc oncogene from the $P_{hCMV^*-1}$ promoter in a tetracycline-regulated fashion (FIG. 1A). The long terminal repeat (LTR) of Moloney murine sarcoma virus transcribed a 7.8 kb mRNA containing both tTA and neomycin phosphotransferase (neo) genes by means of an encephalomyocarditis virus internal ribosome entry site (IRES) (FIG. 1B). The tTA binds to tet operator sequences present in the hybrid promoter in the absence of tetracycline and stimulated transcription from $P_{hCMV^*-1}$ to yield a 3.5 kb mRNA, which produced the v-myc oncoprotein (FIG. 1B). Tetracycline (1 $\mu$g/ml) suppressed the function of the tTA almost completely and inhibited the production of v-myc (FIG. 1C). An amphotropic producer cell line producing LINXv-myc retrovirus was selected and expanded. The virus had a titer of $10^5$ cfu/ml for NIH3T3 cells and did not contain helper viruses.

Example 3

Isolation of Immortalized Neuronal Progenitor Cells

Cultured adult rat hippocampal cells were infected with the LINXv-myc retrovirus and selected for stable transfectants. One culture consisting of several colonies, HC2, showed some cells with neuronal morphology (small phase bright cells with long processes) three days after the addition of 1 $\mu$g/ml of tetracycline. HC2 cells were plated at low density (1:1000) and a single colony was isolated (HC2S2). The same protocol was utilized for infection of fetal progenitor cells, resulting in fetal immortalized neuronal progenitor cells.

Figure 2A:
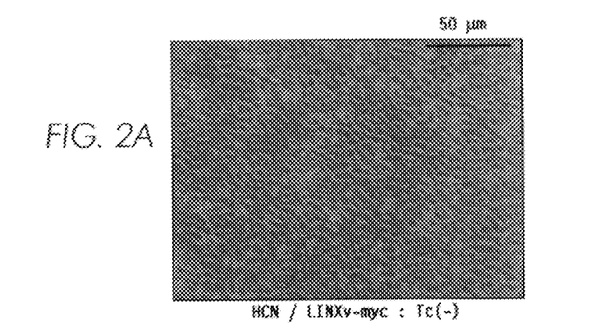
FIGS. 2A and 2B show the a photograph of a culture derived from a single clone (HC2S2) of the adult hippocampal progenitor cells infected with LINXv-myc retrovirus. The HC2S2 cells were grown in the absence of tetracycline for two days (A) and in the presence of tetracycline (1 µg/ml) for three days (B).
Figure 2B:
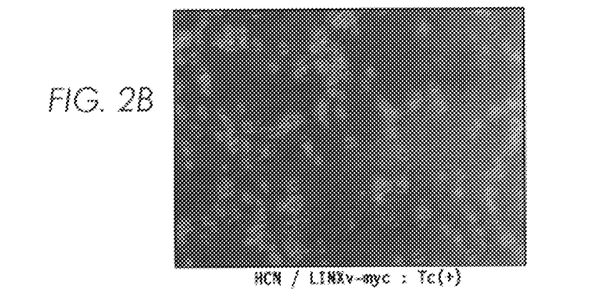
Figure 2C:
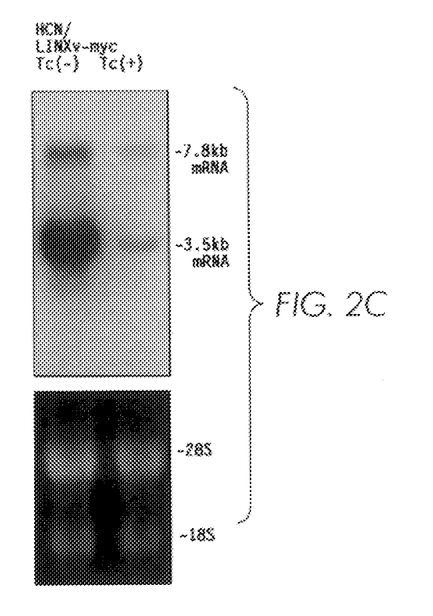
FIG. 2C shows a Northern blot analysis of transcripts from the LTR (7.8 kb mRNA) and the transcripts from $P_{hCMV^{*}1}$ (3.5 kb mRNA) in the HC2S2 cells grown in the absence or presence of tetracycline. The photograph of the gel stained with ethidium bromide is presented as an internal control.

FIG. 2 shows the culture derived from a single clone (HC2S2) of the adult hippocampal progenitor cells infected with LINXv-myc retrovirus. The HC2S2 cells were grown in the absence of tetracycline for two days (2A) and in the presence of tetracycline (1 $\mu$g/ml) for three days (2B). The Northern blot analysis showed the transcripts from the LTR (7.8 kb mRNA) and the transcripts from $P_{hCMV^*-1}$ (3.5 kb mRNA) in the HC2S2 cells grown in the absence or presence of tetracycline (2C). The photograph of the gel stained with ethidium bromide is presented as an internal control.

Figure 3A:
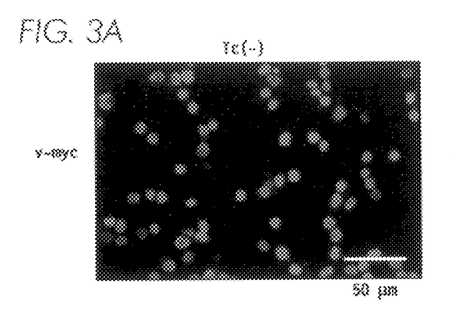
FIGS. 3A–D show immunofluorescence staining for v-myc and BrdU. The HC2S2 cells were grown in the absence of tetracycline (TC) for one day (A, C) and in the presence of tetracycline (1 µg/ml) for two days (D) or three days (B). The cells were stained with anti-v-myc antibody (A, B) or incubated with BrdU for 18 hours and stained with anti-BrdU antibody (C,D).
Figure 3B:
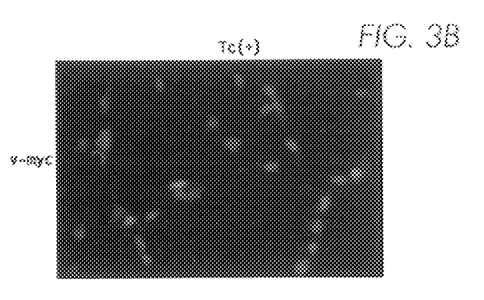
Figure 3C:
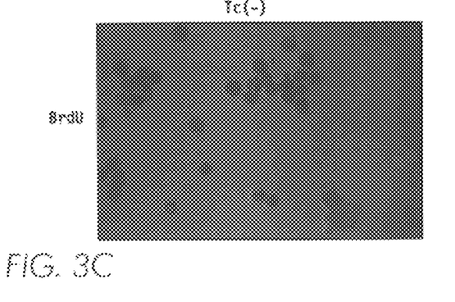
Figure 3D:
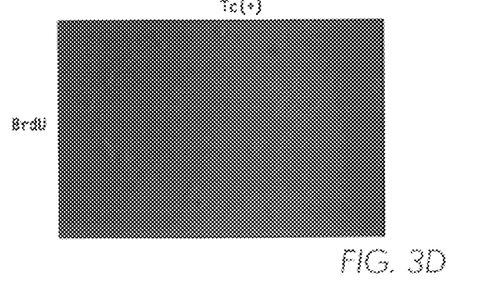

The HC2S2 cells were polygonal and had very small processes (FIG. 2A). Southern blot analysis showed that these cells had a single retroviral genome integration site and therefore can be considered a single clone. The HC2S2 cells grew very rapidly (doubling time of 12 hours) and were not contact inhibited for growth. However, two days after the addition of 1 $\mu$g/ml of tetracycline the cells stopped dividing. Most of the cells became phase-bright and started to extend processes which began to be interconnected by three days after the addition of tetracycline (FIG. 2B). BrdU incorporation studies showed that, when grown in the absence of tetracycline, essentially all HC2S2 cells incorporated BrdU (FIG. 3A). However, tetracycline treatment for two days followed by incubation with BrdU resulted in only 1–2% of the cells incorporating the label (FIG. 3D).

Northern blot analysis showed the production of large amounts of 3.5 kb v-myc transcript in HC2S2 cells grown in the absence of tetracycline. However, amounts of the transcript was reduced after the addition of tetracycline. These results suggested that tetracycline regulates the transcription of v-myc from the hybrid promoter in the HC2S2 cells (FIG. 2C). The transcription from the LTR promoter was also reduced (FIG. 2C). At the protein level, the expression of v-myc oncoprotein in the nucleus of the HC2S2 cells was also down-regulated after the addition of tetracycline (FIG. 3 A, B). Although the suppression of v-myc production by tetracycline was enough to stop proliferation of the HC2S2 cells and induce differentiation, the suppression of the oncogene was not complete.

Example 4

Suppression of the v-myc Production is Sufficient to Differentiate Immortalized Neuronal Progenitor Cells into Neurons The expression of the neural precursor cell markers nestin and vimentin and the neuronal markers tau, NeuN and neurofilament 200 kD protein (NFH) in HC2S2 cells under proliferate and differentiating conditions were examined.

FIG. 3 shows immunofluorescence staining for v-myc and BrdU. The HC2S2 cells were grown in the absence of tetracycline for one day (A, C) and in the presence of tetracycline (1 μg/ml) for two days (D) or three days (B). The cells were stained with anti-v-myc antibody (A, B) or incubated with BrdU for 18 hours and stained with anti-BrdU antibody (C,D).

FIG. 4 shows immunofluorescence staining for neuronal markers. The HC2S2 cells were grown in the absence of tetracycline for one day (A, C, E) and in the presence of tetracycline (1 μg/ml) for five days (B, D, F). The cells were stained with anti-NFH antibody (A, B), anti-tau antibody (C, D), and anti-NeuN antibody (E, F).

Figure 4A:
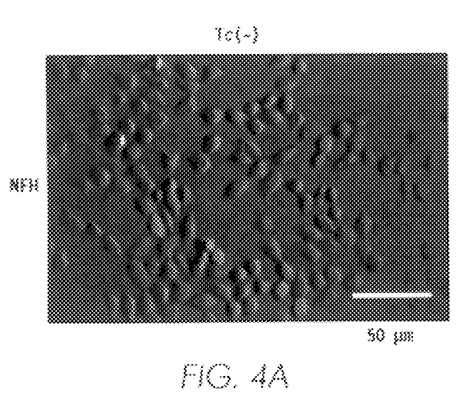
FIGS. 4A–F show immunofluorescence staining for neuronal markers. The HC2S2 cells were grown in the absence of tetracycline for one day (A, C, E) and in the presence of tetracycline (1 µg/ml) for five days (B, D, F). The cells were stained with anti-NFH antibody (A, B), anti-tau antibody (C, D), and anti-NeuN antibody (E, F).
Figure 4B:
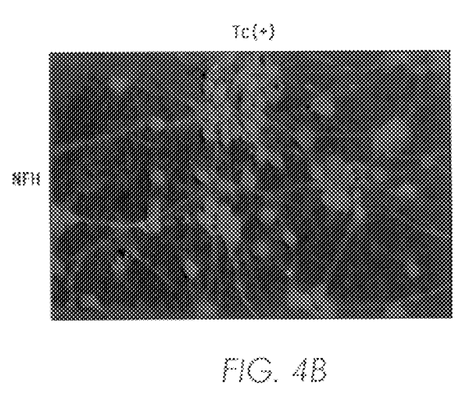
Figure 4C:
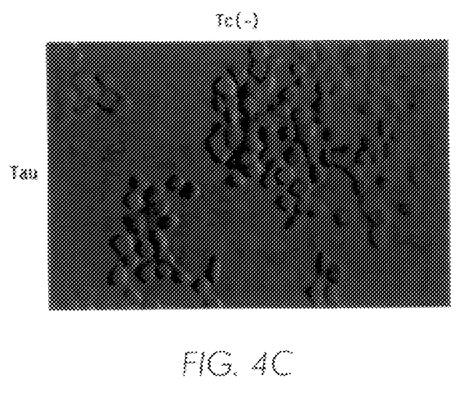
Figure 4D:
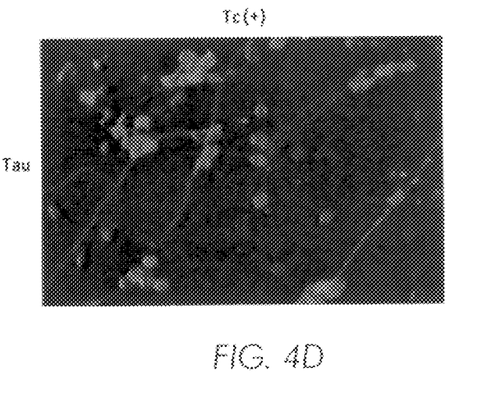
Figure 4E:
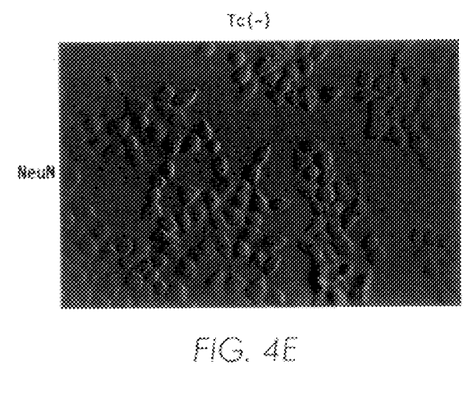
Figure 4F:
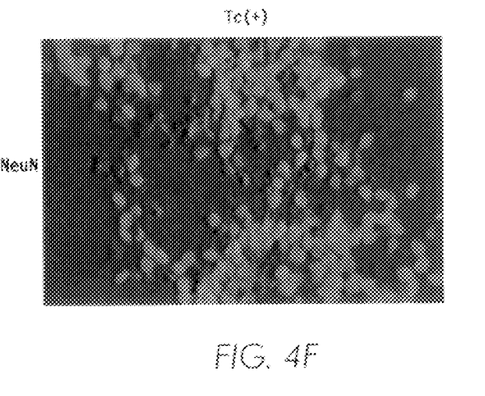

When grown in the absence of tetracycline cells expressed nestin and vimentin. Although a few cells were cytoplasmically stained by the anti-NFH antibody (FIG. 4A), no staining of cells by the anti-tau or anti-NeuN antibodies was observed (FIG. 4C,E). Five days after the addition of tetracycline, almost all cells in culture became positive for NFH, and over half of the cells became positive for tau and NeuN (FIG. 4B, D, F). Cells bodies as well as processes were stained by the anti-NFH and anti-tau antibodies (FIG. 4B,D), and nuclei by the anti-NeuN antibody (FIG. 4F). However, nestin and vimentin staining was no longer present in the cells.

Figure 5:
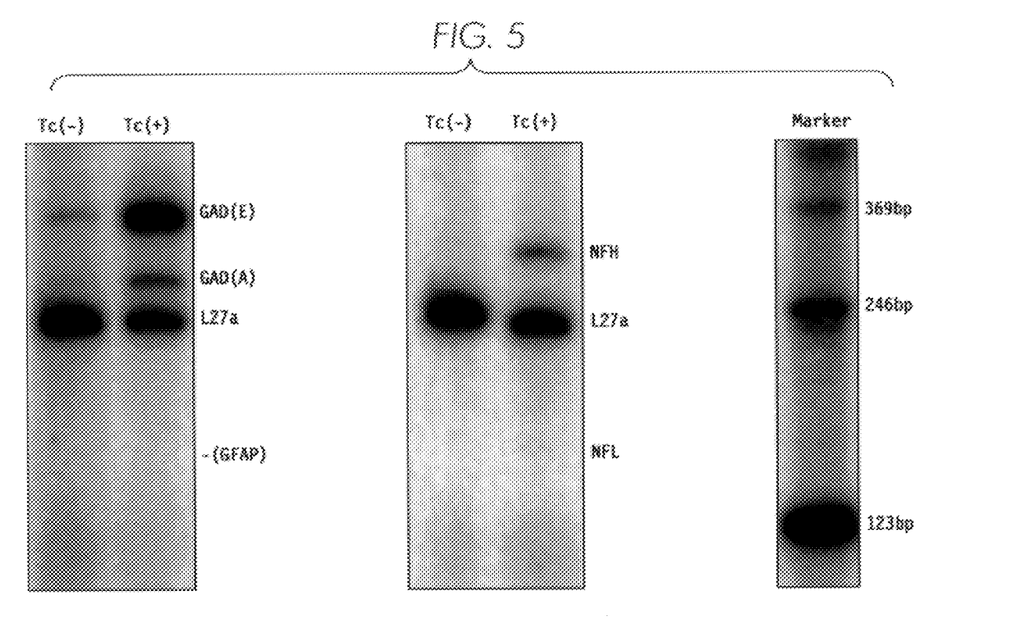
FIG. 5 shows a Northern blot of PCR products of embryonic type of GAD (E) (353 bp), adult type of GAD (A) (267 bp), ribosomal protein L27a (234 bp), GFAP (141 bp), NFH (302 bp), NFL (155 bp) detected in the HC2S2 cells grown in the absence or presence of tetracycline.

FIG. 5 shows PCR products of embryonic type of GAD (E) (353 bp), adult type of GAD (A) (267 bp), ribosomal protein L27a (234 bp), GFAP (141 bp), NFH (302 bp), NFL (155 bp) detected in the HC2S2 cells grown in the absence or presence of tetracycline.

In parallel to the immunological studies, PCR analyses showed the expression of differentiated neural cell markers by HC2S2 cells. Designs for primers predicted PCR products of 234 bp for the ribosomal protein L27a, 267 bp for the adult type of GAD, 353 bp for the embryonic type of GAD, 141 bp for GFAP and 302 bp for NFH. The primer design for GAD can discriminate between the embryonic type of GAD, which is a truncated inactive enzyme, and the adult type of GAD, which is an active enzyme (Bond, et al, *Proc. Natl. Acad. Sci. USA,* 87:8771, 1990). The PCR study demonstrated a marked increase of both types of GAD and mRNA in the differentiated HC2S2 cells three days after the addition of tetracycline (FIG. 4). A very weak NFH PCR product was detected in the HC2S2 cells grown with tetracycline and paralleled finding that only few cells were immunoreactive for anti-NFH. However, there was an increase of the NFH PCR product after the addition of tetracycline (FIG. 5). GFAP mRNA could be detected in cells grown with or without tetracycline (FIG. 5).

Example 5

Immortalized Cells Express Sodium and Calcium Currents after Suppression of v-myc Production Electrophysiological recordings from HC2S2 cells after growth in proliferative and differentiating conditions provided additional evidence that differentiated HC2S2 cells represent neurons.

Figure 6A:
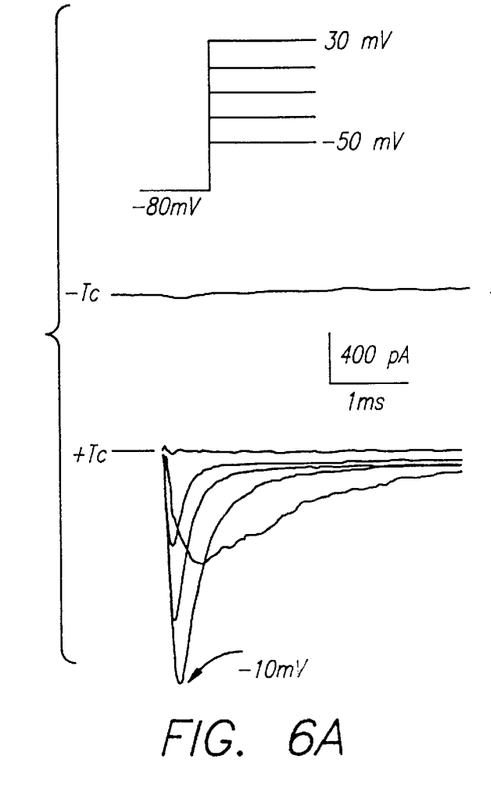
FIG. 6A shows sodium currents elicited by depolarizations from holding potential of −80 mV to test potentials of −50, −30, −10, 10 and 30 mV.
Figure 6B:
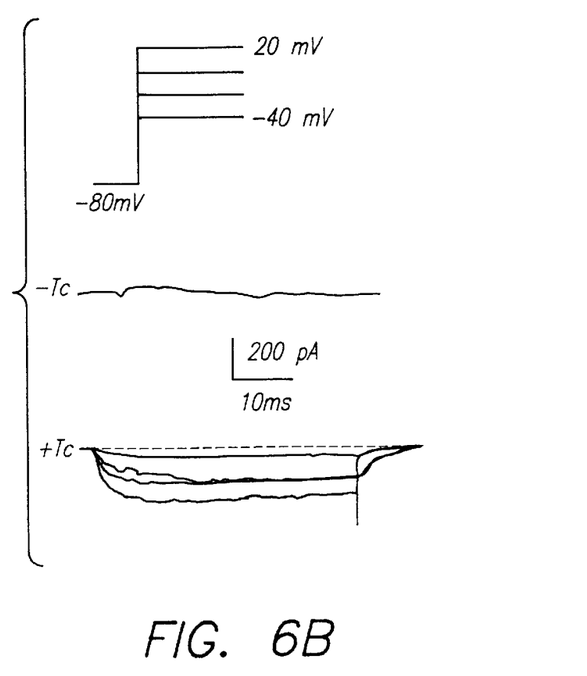
FIG. 6B shows calcium channel currents elicited by depolarizations from a holding potential of −80 mV to test potentials of −40, −20, 0 and 20 mV.
Figure 6C:
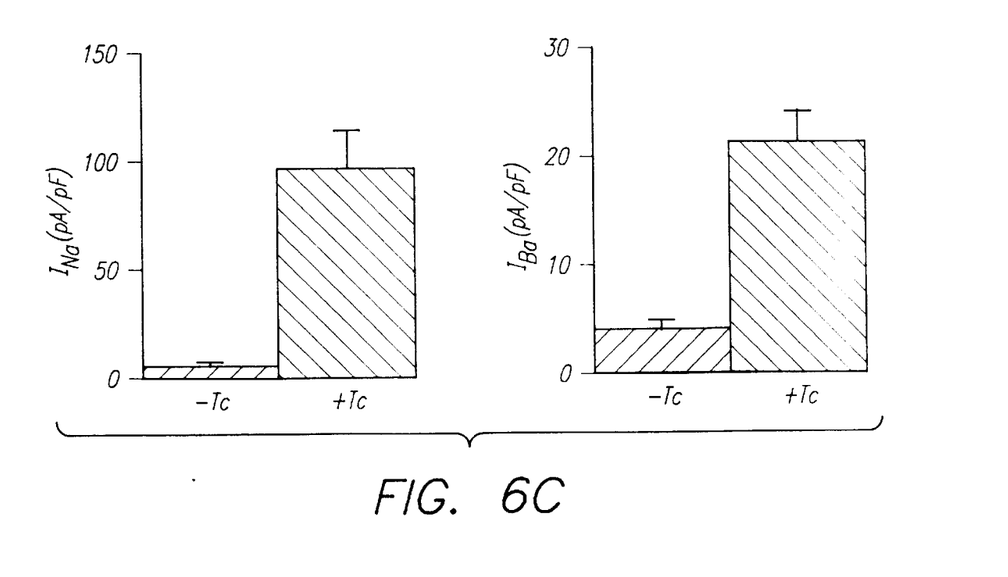
FIG. 6C shows average sodium ($I_{Na}$) and calcium channel ($I_{Ba}$) current densities after growth with or without tetracycline. Current densities are current amplitudes normalized to total cell capacitance. Each bar represents the mean from 16 ($I_{Na}$,+Tc), 12 ($I_{NA}$, −Tc), 10 ($I_{Ba}$, +Tc) or 11 ($I_{Ba}$, −Tc) cells; error bars are S.E.M.s.

FIG. 6 shows HC2S2 cells were grown with FGF-2 at 20 ng/ml, without (−Tc) or with (+Tc) tetracycline for 6 days. Sodium currents elicited by depolarizations from holding potential of −80 mV to test potentials of −50, −30, −10, 10 and 30 mV (6A). Calcium channel currents elicited by depolarizations from a holding potential of −80 mV to test potentials of −40, −20, 0 and 20 mV (6B). Average sodium ($I_{Na}$) and calcium channel ($I_{Ba}$) current densities after growth with or without tetracycline (6C). Current densities are current amplitudes normalized to total cell capacitance. Each bar represents the mean from 16($I_{Na}$, +Tc), 12($I_{NA}$, −Tc), 10($I_{Ba}$, +Tc) or 11($I_{Ba}$, −Tc) cells; error bars are S.E.M.s.

HC2S2 cells examined with whole-cell voltage clamp after growth in proliferative (FGF-2, −Tc) and differentiating (FGF-2+Tc for 6 days) conditions. In proliferative conditions, cells were quiescent, exhibiting virtually no sodium (5±1 pA/pF, 12 cells) or calcium (4±1 pA/pF, 11 cells) current. After growth with tetracycline, substantial sodium and calcium currents were present (FIG. 6A and B; +Tc). The densities of restored sodium and calcium currents (FIG. 6C) were 96±18 pA/pF (16 cells) and 21±3 pA/pF (10 cells), respectively, similar to those present in primary, differentiated fetal rat hippocampal cells in culture. Sodium and calcium currents were activated at potentials more positive than −40 mV, peaked at −10±2 mV (10 cells) and −3±2 mV (4 cells) and reversed at 78±2 mV (8 cells) and 55±9 mV (3 cells) respectively. The restored sodium current in differentiated HC2S2 cells was of the neuronal form, exhibiting a voltage-dependence of inactivation with a midpoint of −60±1 mV (14 cells) and rapid kinetics (time-to-peak of 0.8±0.1 msec, 13 cells). In addition, the restored sodium current was blocked by 1 μM TTX (95±1% inhibition, 6 cells). Concomitant with sodium current induction, HC2S2 cells acquired the ability to fire regenerative action potentials after differentiation with tetracycline.

SUMMARY

The differentiation of HC2S2 cells to neurons was demonstrated by morphological and immunocytochemical characteristics of cells. Neurons with phase-bright cell bodies and interconnected long and thin processes expressing specific neuronal markers, tau, NFH and NeuN were observed. In addition, unlike temperature-sensitive tsA58 immortalized cells, the HC2S2 cells stop expressing nestin upon differentiation (data not shown). Electrophysiology studies have provided further evidence for the differentiation of HC2S2 cells into neurons. Cells treated with tetracycline acquired large sodium currents and the ability to fire action potentials. Moreover, the induced sodium current was of the neuronal form, exhibiting rapid kinetics and a midpoint of inactivation of −61 mV (compared to a midpoint at −80 to −85 mV in glial cells; Barres, et al., *Neuron,* 2:1375, 1989). The restored calcium current was of the high-threshold class, based on the voltage-dependence of activation and lack of inactivation (Bean, et al., *Drugs in development.,* 2:61, 1993). Thus differentiated HC2S2 cells exhibit functional properties essential to CNS neurons: sodium current, which is necessary for initiation and propagation of the action potential, and calcium current, which is required for neurotransmitter release. Taken together, these results suggest that HC2S2 cells were derived from an immortalized neuronal progenitor cell and that they can be differentiated into neurons after the suppression of the v-myc oncogene. Moreover, since these cells are derived from the adult hippocampus, progenitor cells with the potential for neuronal differentiation must exist in the adult nervous system and they are amenable to isolation and expansion in vitro. It is now possible to study the mechanism of the cell cycle arrest and subsequent differentiation into neurons that is induced by the down-regulation of the over expressed v-myc oncogene.

What is claimed is:

1. A retroviral vector comprising nucleic acid encoding:
   a regulatable tetracycline controlled tansactivator (tTA) element and a selectable marker separated by an internal ribosome entry site (IRES), wherein a viral long terminal repeat (LTR) transcribes both the tTA element and the selectable marker,
   a heterologous gene; and
   a regulatory element containing tet operator (tet O) sequences, wherein the regulatory element is in operable linkage with the heterologous gene.

2. The vector of claim 1, wherein the regulatory element in operable linkage to the heterologous gene is a promoter.

3. The vector of claim 2, wherein the promoter in operable linkage to the heterologous gene is a human cytomegalovirus (hCMV) promoter.

4. The vector of claim 1, wherein the heterologous gene is an oncogene.

5. The vector of claim 4, wherein the oncogene is v-myc.

6. The vector of claim 1, wherein the selectable marker is selected from the group consisting of aminoglycoside phosphotransferase, dihydrofolate reductase (DHFR), hygromycin-B-phosphotransferase (HPH), thymidine kinase (TK), and xanthine guanine phosphoribosyltransferse (XGPRT, gpt).

7. The vector of claim 1, wherein the vector is ATCC 6999.

8. A method of producing a recombinant retrovirus comprising transfecting a suitable packaging host cell with the vector of claim 1 and recovering the recombinant virus.

9. A recombinant retrovirus produced by the method of claim 8.

10. A cell comprising the retrovirus of claim 9.

11. The cell of claim 10, wherein the cell is a neuronal progenitor cell.

12. The cell of claim 11, wherein the cell is ATCC CRL 12402.

13. A method for inducing differentiation of a neural cell comprising infecting a neural progenitor cell with the recombinant retrovirus of claim 9 and growing the cell under conditions and for a suitable time to allow the cells to differentiate.

14. A method for introduction and expression of a heterologous nucleic acid sequence in a neural progenitor cell comprising infecting the cell with the recombinant virus of claim 9 and expressing the heterologous nucleic acid sequence in the cell.

15. The method of claim 14, wherein the heterologous nucleic acid sequence is an oncogene.

16. The method of claim 15, wherein the oncogene is v-myc.

17. A cell producing recombinant retrovirus wherein the cell is produced by the method of claim 8.

18. A cell comprising the vector of claim 1.

19. A cell line having a ATCC accession number CRL 12402.

* * * * *